United States Patent [19]

Tsugita et al.

[11] Patent Number: 5,538,896
[45] Date of Patent: Jul. 23, 1996

[54] HIGHLY SENSITIVE DETECTION METHOD OF AMINO ACID DERIVATIVE

[75] Inventors: Akira Tsugita, Kashiwa; Masaharu Kamo, Noda; Mitsuru Sano, Kurashiki, all of Japan

[73] Assignees: Seiko Instruments Inc.; Kurabo Industries Ltd., both of Japan

[21] Appl. No.: 211,339

[22] PCT Filed: Jun. 2, 1993

[86] PCT No.: PCT/JP93/00744

§ 371 Date: May 9, 1994

§ 102(e) Date: May 9, 1994

[87] PCT Pub. No.: WO94/02854

PCT Pub. Date: Feb. 3, 1994

[30] Foreign Application Priority Data

Jul. 27, 1992 [JP] Japan .................................. 4-199684

[51] Int. Cl.[6] ............................................... G01N 33/00
[52] U.S. Cl. .......................... 436/89; 436/161; 436/172; 530/405; 530/409

[58] Field of Search ............................ 436/86, 89, 161, 436/172; 530/405, 409

[56] References Cited

U.S. PATENT DOCUMENTS 4,865,994  9/1989  Tsugita et al. ............................ 436/57
5,051,369  9/1991  Tsugita et al. ............................ 436/89

Primary Examiner—David A. Redding
Attorney, Agent, or Firm—Adams & Wilks

[57] ABSTRACT

To easily detect an amino acid derivative with high sensitivity in carrying out amino acid sequence analysis of a protein from an amino terminal, 2-anilino-5-thiazolinone amino acid derivative is reacted with a volatile primary amine represented by the general formula $X-NH_2$, wherein X denotes a hydrocarbon containing a halogen to form a phenylthiocarbamyl amino acid derivative, and the phenylthiocarbamyl amino acid derivative is detected by using a gas chromatograph provided with an ECD. Accordingly, amino acid sequencing may be performed with high sensitivity without the need to use harmful radioisotope labeled or fluorescent amino compounds.

2 Claims, 5 Drawing Sheets

HIGHLY SENSITIVE DETECTION METHOD OF AMINO ACID DERIVATIVE

TECHNOLOGICAL FIELD

The present invention relates to an analysis method of amino acid sequence from an amino (N) terminal of protein.

BACKGROUND TECHNOLOGY

As shown in FIG. 2, for identification of an amino acid derivative in the last stage of Edman degradation, which is a sequence analysis method of a protein from the N terminal, protein is conventionally reacted with phenylisothiocyanate (PITC) to obtain phenylthiocarbamyl (PTC) protein, which is treated with an acid to produce 2-amino-5-thiazolinone (ATZ) amino acid derivative, which is further treated with an acid to form phenylthiohydantoin (PTH) amino acid derivative, which is detected by ultraviolet absorption spectroscopy as a known analysis method (P. Edman, Acta Chem. Scand. 10, 761 (1956)).

Further, another method is disclosed in Japanese Patent Application Laid-Open No. 61-264264, and shown herein in FIG. 3, in which an ATZ amino acid derivative is reacted with an amino compound labeled with a radioactiveisotope to form a PTC amino acid derivative, which is separated by thin-layer chromatography for detection.

Moreover, still another method is disclosed in Japanese Patent Application Laid-Open No. 63-196858 and shown in FIG. 4 herein in which an ATZ amino acid derivative is reacted with a fluorescent amino compound to form a PTC amino acid derivative, which is separated by high speed liquid chromatography for detection.

With regard to the conventional method of detecting the PTH amino acid derivative by ultraviolet absorption spectroscopy, while the detecting means is rather simple, this sequencing method is not suitable for the highly sensitive analysis which is recently demanded for treating a trace amount of protein or very trace amount of peptide.

Further, with regard to the developed highly sensitive analysis method utilizing the amino compound labeled with the radioactiveisotope, this has rather limited application in view of ill effects to the environment and, in particular, to the human body.

Moreover, with regard to the other developed highly sensitive analysis method utilizing the fluorescent amino compound, it is necessary to add a large quantity of a fluorescent reagent for maintaining a reaction rate when treating a trace amount of sample in such a liquid phase reaction. Further, it is known that the reaction yield rate decreases as a density of the sample, i.e., the ATZ derivative of protein or peptide decreases even though a large quantity of the reactive reagent is added. In such a case, the excess fluorescent amino compound which remains after the reaction with the ATZ amino acid derivative disturbs quantitative analysis of the product. Further, since the fluorescent compound is nonvolatile, it is complicated to remove the same after the reaction with the ATZ amino acid derivative.

In view of this, an object of the present invention is to provide a new method of promoting a high yield rate reaction to readily obtain the PTC amino acid derivative for highly sensitive detection.

SUMMARY OF THE INVENTION

For solving the above noted drawback, according to the present invention, in order to analyze the amino acid sequence from an N terminal of a protein, an ATZ amino acid derivative is reacted with a volatile primary amine represented by a general formula $X-NH_2$ (X denotes a hydrocarbon containing a halogen) to thereby produce a PTC amino acid derivative. Then, the PTC amino acid derivative is detected by a gas chromatograph provided with an electron capture detector (ECD).

By this means, the high yield rate reaction is promoted to readily detect the PTC amino acid derivative with a high degree of sensitivity.

DETAILED DESCRIPTION OF THE PREFERRED EMBODIMENTS

The detailed description is given for the invention in conjunction with the attached drawings. The embodiment 1 indicates that the detection sensitivity of an amino acid derivative is significantly high according to the invention.

Figure 1:
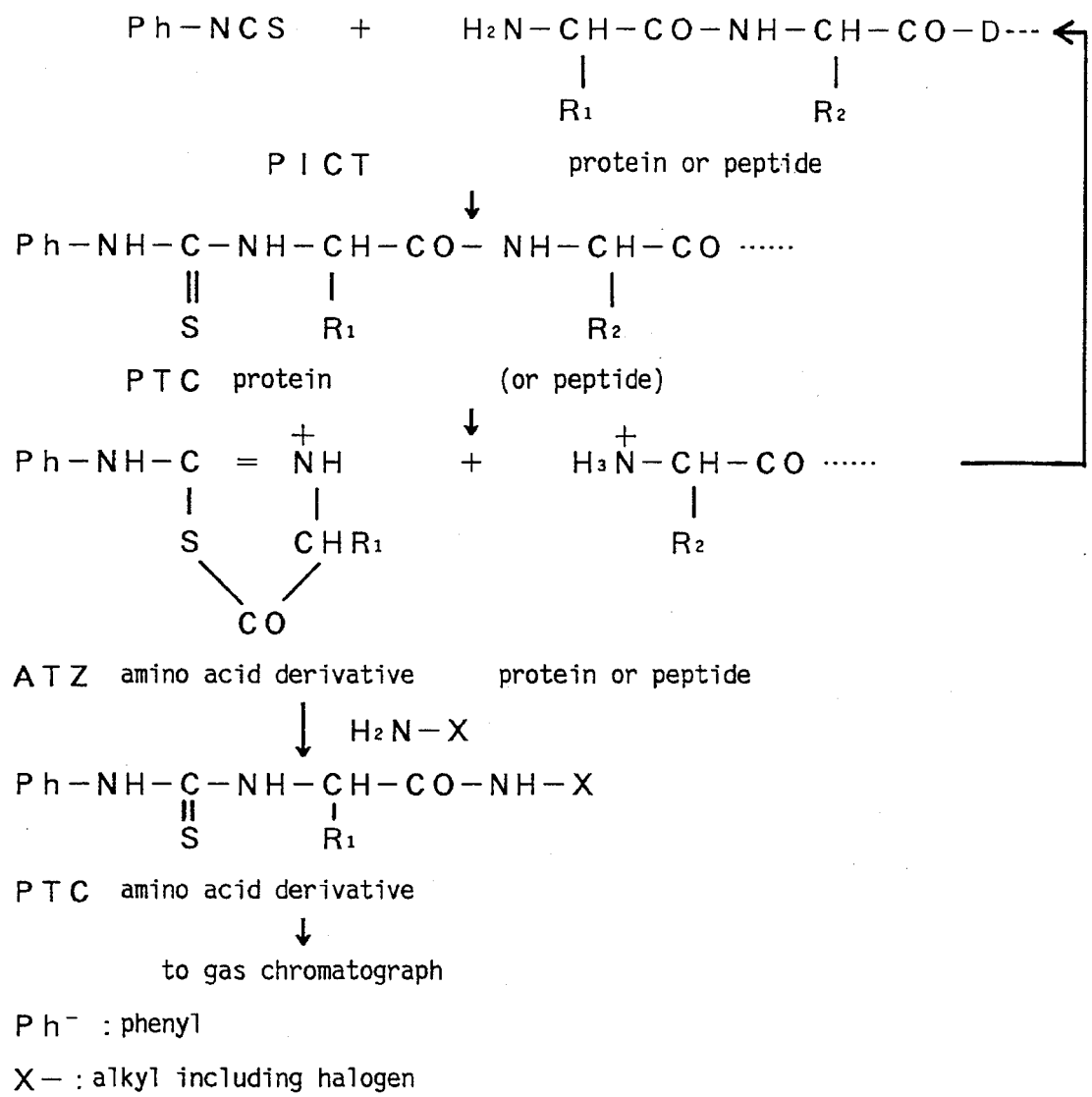
FIG. 1 is a step diagram showing the inventive analysis method.
Figure 2:
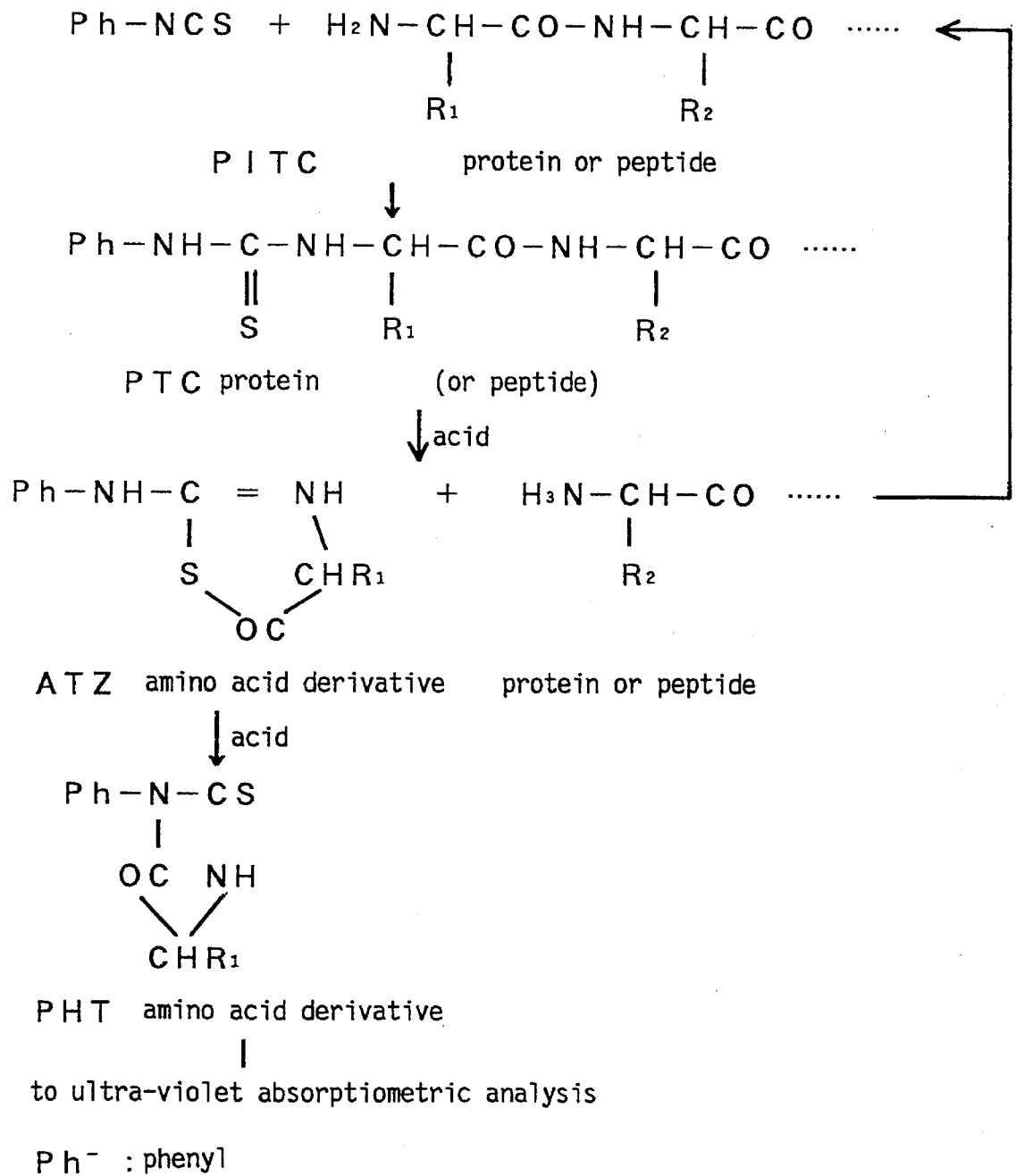
FIG. 2 shows one conventional analysis method of detection by ultraviolet absorption spectroscopy.
Figure 3:
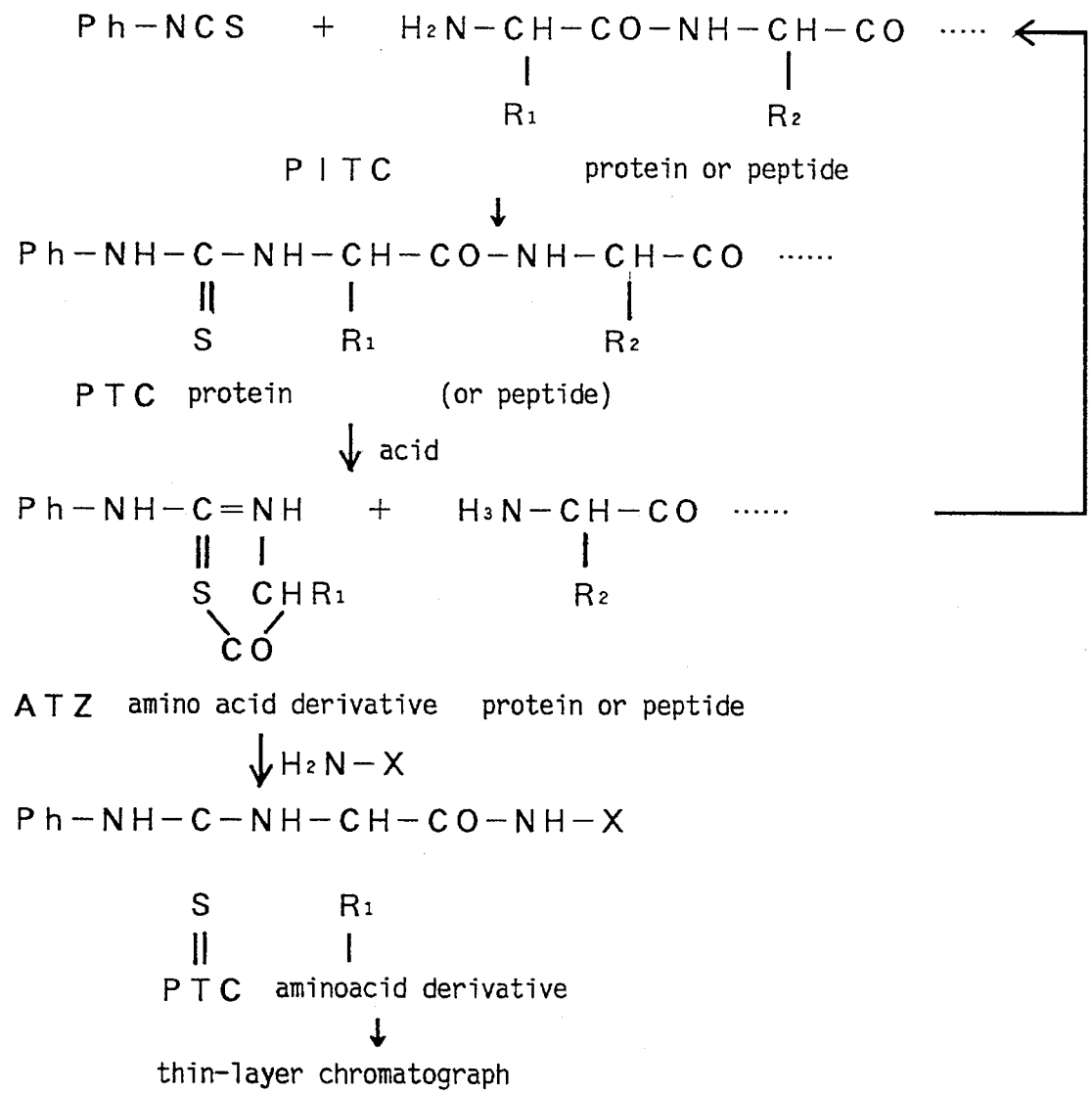
FIG. 3 shows another conventional analysis method utilizing an amino compound labeled with a radioactiveisotope.
Figure 4:
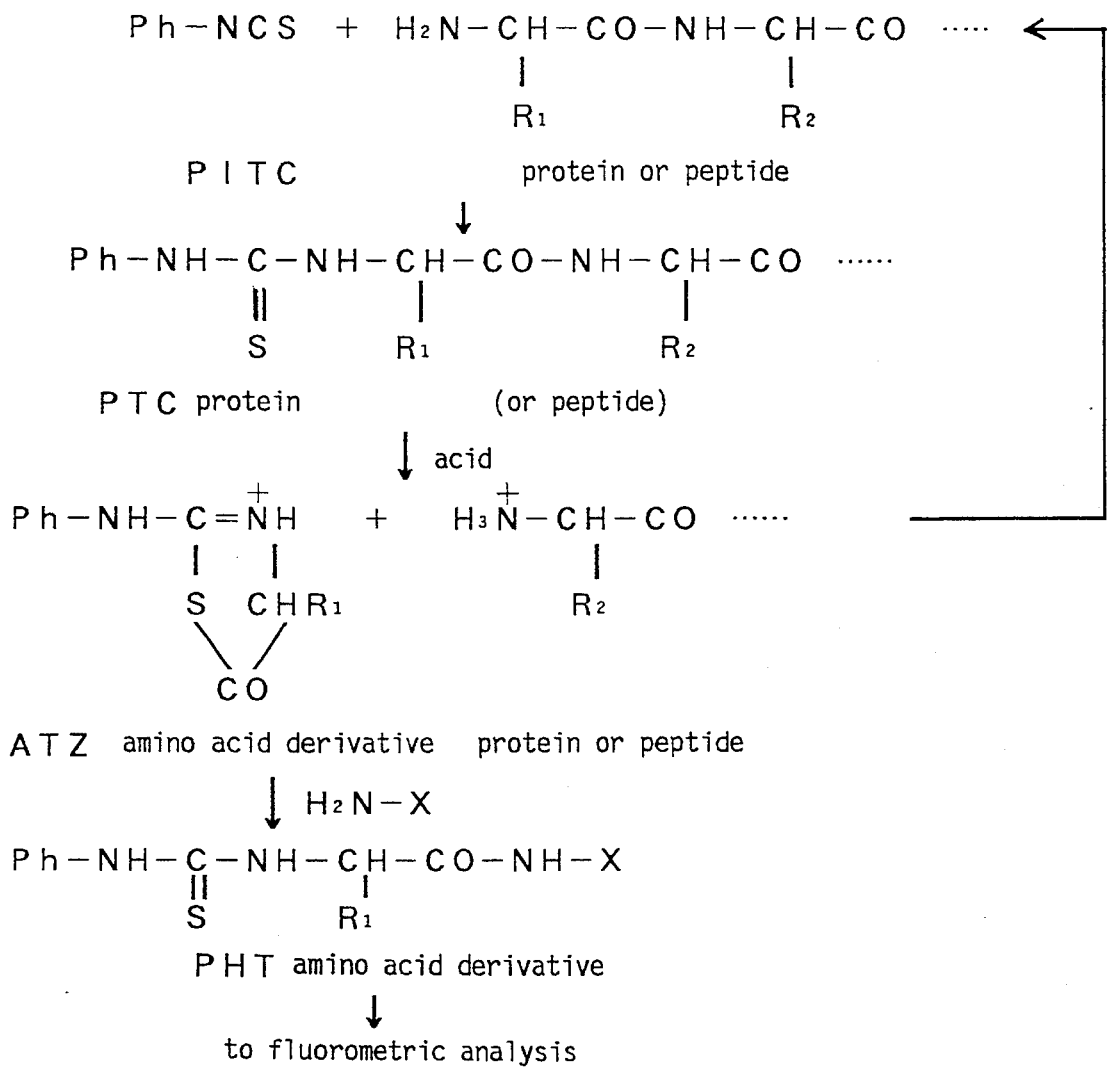
FIG. 4 shows a still another conventional analysis method utilizing a fluorescent amino compound.

First, FIG. 1 shows steps of the inventive method. An amino compound of hydrocarbon containing a halogen is applied to an ATZ amino acid derivative obtained by a process based on Edman degradation to form a PTC amino acid derivative. Next, this PTC amino acid derivative is identified by a gas chromatograph provided with an ECD.

The PTC phenylalanine amino acid derivative is prepared by the following steps. First, a dipeptide of Phe-Gly is subjected to Edman degradation to obtain an ATZ phenylalanine derivative. This process of the Edman degradation is known, and is therefore not described in detail here. Then, the ATZ phenylalanine derivative is filled in a test tube of φ4×40 mm, and is dried. This test tube is then placed into another test tube of φ13×100 mm provisionally filled with 100 μl of 2,2,2-trifluoroethylamine (TFEA). The outer test tube is vacuum-sealed to carry out a reaction for 20 minutes at 80° C. After opening the test tube, an excess of TFEA is removed by blow of nitrogen gas.

Figure 5:
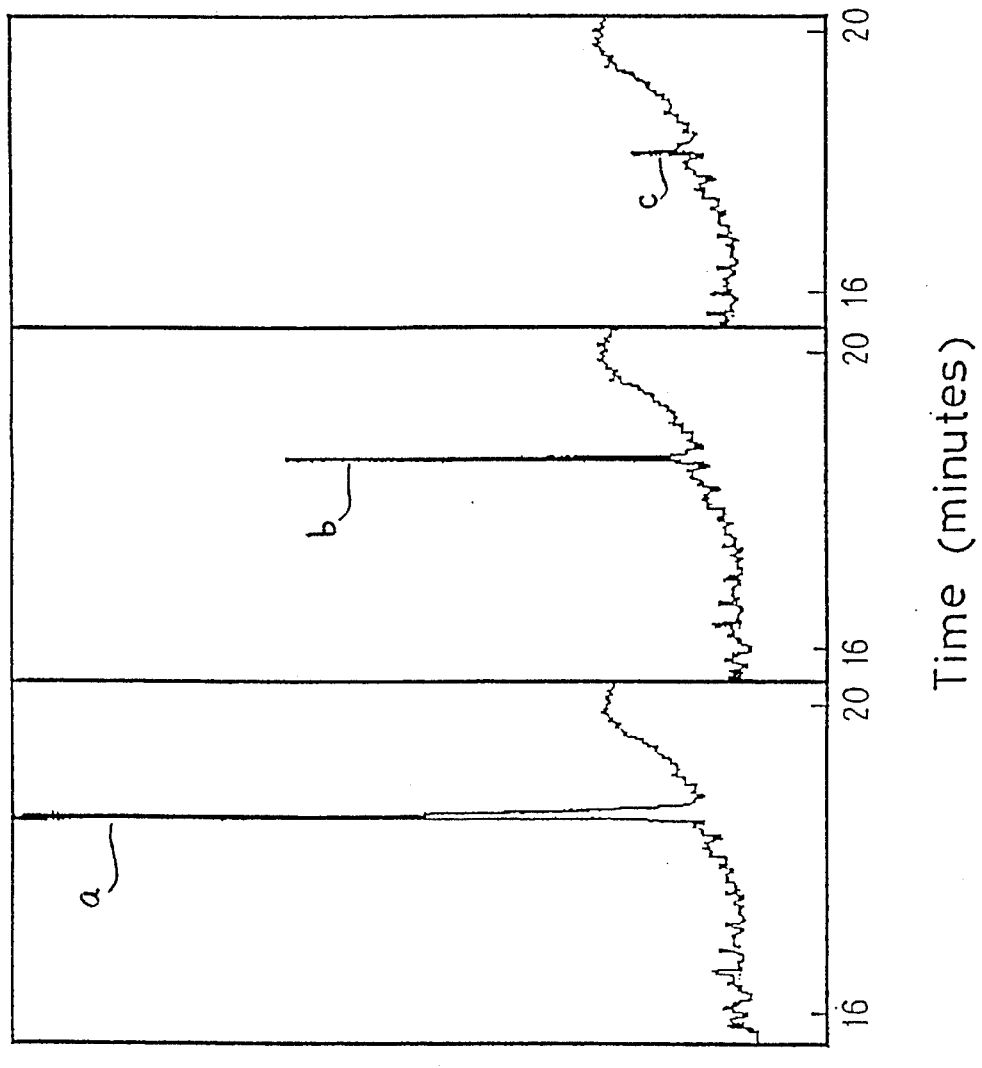
FIG. 5 shows a gas chromatograph for detecting a PTC phenylalanine derivative, where (a), (b) and (c) show analysis results of the PTC phenylalanine derivative in the amounts of 5 pmol, 500 fmol and 50 fmol, respectively.

FIG. 5 is a gas chromatograph for detecting the PTC phenylalanine amino acid derivative prepared under the above described conditions. The gas chromatography is carried out according to the following condition.

| | |
|---|---|
| Instrument (detector) | HP5890 (ECO) |
| Carrier gas (flow rate) | helium (1.5 ml/minute) |
| Column | ULTRA #2 (crosslinked 5% phenylmethyl silicone) length 25 m, internal diameter 0.32 mm, film thickness 0.17 μm |
| Oven temperature | Initial temp. 50° C. 1 minute Rinsing rate 10° C./minute End temp. 300° C. 15 minutes |
| Inlet opening temperature | 250° C. |
| Detector temperature | 300° C. |

A peak (a) is obtained when 5 pmol of the sample PTC phenylalanine derivative is analyzed, another peak (b) is obtained when 500 fmol is analyzed, and still another peak (c) is obtained when 50 fmol is analyzed. Based on these results, the detection limit of the present invention is compared with that of the conventional method utilizing the PTH derivative (PTH method). As shown in the Table 1, the detection sensitivity of the invention is extremely high (1 pmol=1×10$^{-12}$ mol, 1 fmol=1×10$^{-15}$ mol).

TABLE 1

| Detection method | Detection limit |
| --- | --- |
| PTH method | 1 pmol |
| Inventive method | 50 fmol or less |

The embodiment 2 shows that reaction yield rate between ATZ derivative and TFEA is high in the inventive highly sensitive detection method of the amino acid derivative. In this embodiment, a dipeptide of Phe-Gly is used. The PTC phenylalanine derivative is prepared in the same manner as the embodiment 1. In this embodiment, the PTC phenylalanine derivative is analyzed by using a micro-bore fast liquid chromatography (HPLC).

The used condition of HPLC is as follows.

HPLC instrument: Applied Biosystems 130A

Column: Applied Biosystems Spheri-5RP-18 (φ1.0 mm×50 mm)

Eluent: 32% acetonitrile containing 0.1% trifluoroacetic acid

Column temperature: 55° C.

Detection wave length: 254 nm

Table 2 shows a yield of the PTC phenylalanine while the quantity of ATZ derivative is varied.

TABLE 2

| Quantity of ATZ derivative | Yield | |
| --- | --- | --- |
| (pmol) | (pmol) | (%) |
| 100 | 85 | 85 |
| 10 | 8.5 | 85 |
| 1 | 0.81 | 81 |
| 0.15 | 0.078 | 78 |
| 0.05 | 0.035 | 70 |

As shown, even though the starting material is 50 fmol, a yield of 70% can be obtained such that the reactivity is maintained for analyzing a trace amount of sample. In the conventional method of using the PTH derivative, the reaction yield rate of the ATZ derivative is 40% at 1 pmol, 10% at 100 fmol and 4% at 50 fmol.

An object of the present invention is to provide a highly sensitive and detection of an amino acid derivative in the amino acid sequence analysis of protein or peptide from the N terminal.

According to a significant aspect of the present invention, in order to analyze an amino acid sequence of protein from an amino terminal, an ATZ amino acid derivative is reacted with a volatile primary amine represented by a general formula X-NH$_2$ (X denotes a hydrocarbon containing halogen) to produce a PTC amino acid derivative. The PTC amino acid derivative is detected by a gas chromatograph provided with an ECD. By this, novel process the high yield reaction is promoted to realize highly sensitive and ready detection of the amino acid derivative. In such a reaction system, the sample is reacted with the reactive reagent composed of the primary amine having the volatile nature, which facilitates removal of an excess the reagent after the reaction. The highly sensitive detection method of the amino acid derivative according to the invention has a great industrial value.

We claim:

1. A highly sensitive detection method of an amino acid derivative, comprising: reacting 2-anilino-5-thiazolinone amino acid derivative with a volatile primary amine represented by the general formula X-NH$_2$, wherein to produce a phenylthiocarbamyl amino acid derivative, and detecting the phenylthiocarbamyl amino acid derivative by a gas chromatograph provided with an electron capture detector.

2. A highly sensitive detection method of an amino acid derivative according to claim 1, wherein the 2-anilino-5-thiazolinone amino acid derivative is obtained by Edman degradation in which a protein or a peptide is reacted with a phenylisothiocyanate to produce a phenylthiocarbamyl protein or a phenylthiocarbamyl, which is thereafter reacted with an acid.

* * * * *